(12) United States Patent
Zheng et al.

(10) Patent No.: US 12,409,037 B1
(45) Date of Patent: Sep. 9, 2025

(54) DELIVERY SYSTEM FOR VALVE REPAIR

(71) Applicant: Creative Medtech (Suzhou) Co., Ltd., Jiangsu (CN)

(72) Inventors: Wei Zheng, Beijing (CN); Shuqi Li, Beijing (CN); Wuen Han, Beijing (CN); Meiyu Song, Beijing (CN)

(73) Assignee: Creative Medtech (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 19/173,802

(22) Filed: Apr. 8, 2025

(30) Foreign Application Priority Data

Oct. 25, 2024 (CN) .................. 202411495978.X

(51) Int. Cl.
*A61F 2/24* (2006.01)

(52) U.S. Cl.
CPC .......... *A61F 2/2466* (2013.01); *A61F 2/2427* (2013.01); *A61F 2/2436* (2013.01); *A61F 2/2454* (2013.01); *A61F 2220/0016* (2013.01)

(58) Field of Classification Search
CPC .... A61F 2/2427; A61F 2/2436; A61F 2/2439; A61F 2/2466
See application file for complete search history.

(56) References Cited

FOREIGN PATENT DOCUMENTS

| CN | 109498216 A | 3/2019 |
|----|-------------|--------|
| CN | 110313947 A | 10/2019 |
| CN | 111358509 A | 7/2020 |
| CN | 111568605 A | 8/2020 |
| CN | 212234802 U | 12/2020 |
| CN | 115153958 A | 10/2022 |
| CN | 115245407 A | 10/2022 |
| CN | 115281893 A | 11/2022 |
| CN | 117462303 A | 1/2024 |
| WO | 2022143141 A1 | 7/2022 |
| WO | 2024139057 A1 | 7/2024 |

OTHER PUBLICATIONS

Notice of Allowance of counterpart Chinese Patent Application No. 202411495978.X issued on Dec. 11, 2024.
First Office Action of counterpart Chinese Patent Application No. 202411495978.X issued on Nov. 30, 2024.

*Primary Examiner* — William H Matthews

(57) ABSTRACT

A delivery system for valve repair is provided, and relates to the technical field of valve repair. The first delivery assembly includes a first wire locker control device and a first nailing control device, one end of the first wire locker control device is fixedly connected with the multi-lumen tube, and the other end is detachably connected with the first nailing control device; the second delivery assembly is detachably connected with the first wire locker control device. The second delivery assembly includes a second wire locker control device and a second nailing control device. The multi-lumen tube internally includes a first lumen tube, a second lumen tube and a third lumen tube which are axially arranged.

10 Claims, 6 Drawing Sheets

DELIVERY SYSTEM FOR VALVE REPAIR

CROSS-REFERENCE TO RELATED APPLICATION

This application is based on and claims priority under 35 U.S.C. 119 to Chinese Patent Application No. 202411495978.X, filed on Oct. 25, 2024, in the China National Intellectual Property Administration. The entire disclosure of the above application is incorporated herein by reference.

TECHNICAL FIELD

The disclosure relates to the technical field of valve repair, in particular to a delivery system for valve repair.

BACKGROUND

Heart valves are barriers between different cardiovascular structures. They can only open and close in a certain direction to ensure that blood can only flow forward and not backward. The mitral valve is a "one-way valve" between the left atrium and the left ventricle, ensuring that blood circulation flows from the left atrium to the left ventricle in a directional manner and passes a certain amount of blood flow. Blood flows from the left atrium through the mitral valve into the left ventricle, and is then pumped into the aorta by the left ventricle and flows to the whole body. The mitral valve is opened, and blood flows from the left atrium into the left ventricle. Then the mitral valve is closed to ensure that when the left ventricle contracts to pump blood to the aorta, blood does not flow back into the left atrium. If the mitral valve is diseased and cannot be fully closed, it will cause blood to flow back into the left atrium when the left ventricle contracts. This is mitral regurgitation.

The mitral regurgitation is the most common heart valve disease worldwide. Regurgitation reduces blood flow to various parts of the body. In order to compensate, the heart will try to pump blood more forcefully, which increases the workload of the heart. Patients with severe mitral regurgitation may experience a variety of debilitating symptoms, such as shortness of breath, palpitations, dizziness and fatigue. These patients face the risk of poor quality of life, significant limitation of activities, repeated hospitalizations due to heart failure and increased mortality. Chronic severe mitral regurgitation is often accompanied by heart failure, which can lead to death if not treated.

SUMMARY

The delivery system for valve repair of the present disclosure includes:
  a first delivery assembly and a second delivery assembly;
  the first delivery assembly includes a first wire locker control device and a first nailing control device, one end of the first wire locker control device is fixedly connected to a multi-lumen tube, and the other end of the first wire locker control device is detachably connected to the first nailing control device, the first nailing control device is configured to control a first nailing device to nail, and the first wire locker control device is configured to control a first wire locker to lock the first nailing device;
  the second delivery assembly is detachably connected to the first wire locker control device, the second delivery assembly includes a second wire locker control device and a second nailing control device, the second nailing control device is configured to control a second nailing device to nail, and the second wire locker control device is configured to control a second wire locker to lock the second nailing device;
  the second wire locker control device is arranged on a housing of the second nailing control device, and the second nailing control device is detachably connected to the first wire locker control device; based on that the second nailing control device is connected to the first wire locker control device, the first nailing control device is detached from the first wire locker control device;
  the multi-lumen tube includes a first lumen, a second lumen and a third lumen which are arranged axially, the first lumen is used for the first wire locker to enter, the second lumen is used for the first nailing device and the second nailing device to enter respectively, and the third lumen is used for the second wire locker to enter;
  the delivery system for valve repair is configured to enable the first wire locker and the second wire locker to synchronously lock the first nailing device and the second nailing device through the first lumen and the third lumen.

The delivery system for valve repair of the present disclosure further includes a sheath tube bending-adjustment assembly;
  the sheath tube bending-adjustment assembly includes a first mounting bracket and a first adjustment structure, wherein the first adjustment structure is arranged on a side of the first mounting bracket for adjusting a bending of a sheath tube, one end of the first mounting bracket is connected to the sheath tube, and the other end of the first mounting bracket is connected to the first wire locker control device;
  the multi-lumen tube passes through the first mounting bracket and passes through the sheath tube.

In the delivery system for valve repair, the first wire locker control device includes a second mounting bracket and a second adjustment structure, one end of the second mounting bracket is connected to the multi-lumen tube, and the other end of the second mounting bracket is connected to the first nailing control device or the second delivery assembly, the second adjustment structure is fixedly connected to a side of the second mounting bracket, and the second adjustment structure is configured to control an axial movement and a circumferential rotation of the first wire locker;
  the first wire lock passes through the second adjustment structure and the second mounting bracket in sequence.

In the delivery system for valve repair, the first nailing control device includes a third mounting bracket and a third adjustment structure, one end of the third mounting bracket is connected to the second mounting bracket, and the other end of the third mounting bracket is connected to the third adjustment structure;
  the first nailing device passes through the third adjustment structure, the third mounting bracket and the second mounting bracket in sequence, and the third adjustment structure is configured to control an axial movement and a circumferential rotation of the first nailing device.

In the delivery system for valve repair, the second nailing control device includes a fourth mounting bracket and a fourth adjustment structure, one end of the fourth mounting bracket is connected to the second mounting bracket, and the other end of the fourth mounting bracket is connected to the fourth adjustment structure and the second wire locker control device;

the second nailing device passes through the fourth adjustment structure, the fourth mounting bracket and the second mounting bracket in sequence, and the fourth adjustment structure is configured to control an axial movement and a circumferential rotation of the second nailing device.

In the delivery system for valve repair, the second wire locker control device includes a fifth adjustment structure, and the fifth adjustment structure is connected to the fourth mounting bracket;

the second wire locker passes through the fifth adjustment structure, the fourth mounting bracket and the second mounting bracket in sequence, and the fifth adjustment structure is configured to control an axial movement and a circumferential rotation of the second wire locker.

In the delivery system for valve repair, a first limiting hole is arranged on a side wall of the second mounting bracket, the first limiting hole penetrates the side wall of the second mounting bracket, a first limiting groove is arranged on a side wall of the third mounting bracket, and a second limiting groove is arranged on a side wall of the fourth mounting bracket;

based on that the third mounting bracket or the fourth mounting bracket is connected to the second mounting bracket, a first limiting member is inserted into the first limiting groove or the second limiting groove through the first limiting hole, and the first limiting member is configured to limit a movement of the third mounting bracket or a movement of the fourth mounting bracket.

The delivery system of valve repair further includes a dilation tube, wherein the dilation tube is detachably connected to the sheath tube bending-adjustment assembly.

In the delivery system for valve repair, injection channels are respectively arranged on the second mounting bracket, the third mounting bracket and the fourth mounting bracket, and the injection channels are configured to inject sealing liquid to seal an internal space of the multi-lumen tube.

In the delivery system for valve repair according to claim 5, observation windows are respectively arranged on the third mounting bracket and the fourth mounting bracket, and the observation windows are made of transparent material.

BRIEF DESCRIPTION OF FIGURES

Other features, objects and advantages of the present disclosure will become more apparent by reading the detailed description of non-limiting embodiments made with reference to the following drawings.

DETAILED DESCRIPTION

Figure 1:
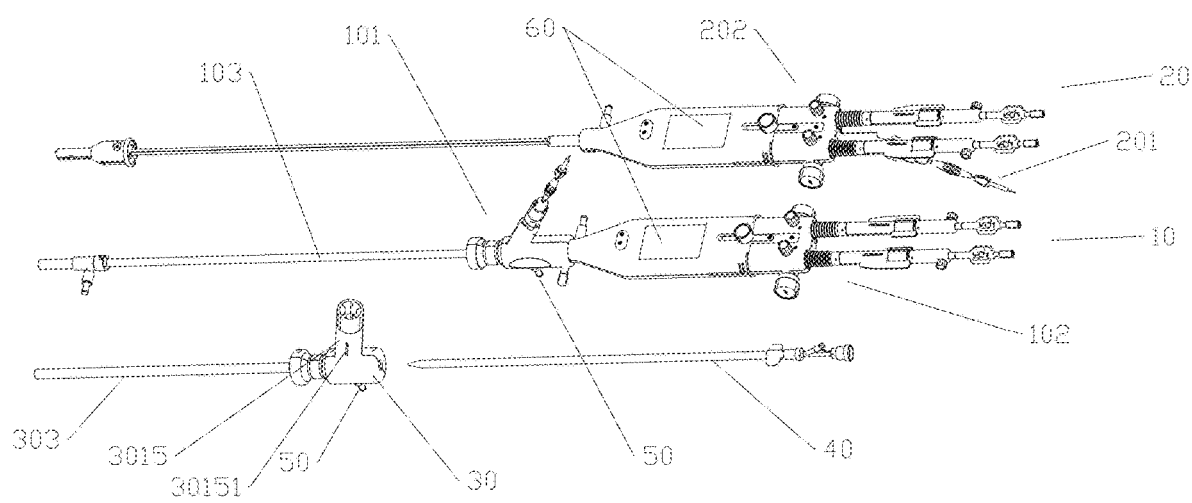
FIG. 1 schematically shows a schematic diagram of a structure of a delivery system according to an embodiment of the present disclosure.

In order to make the purpose, technical solution and advantages of the embodiments of the present disclosure clearer, the technical solution in the embodiments of the present disclosure will be clearly and completely described below in conjunction with the drawings in the embodiments of the present disclosure. Obviously, the described embodiments are part of the embodiments of the present disclosure, not all of the embodiments. Based on the embodiments of the present disclosure, all other embodiments obtained by ordinary technicians in this field without creative work are within the scope of protection of the present disclosure.

The terms used in the embodiments of the present disclosure are only for the purpose of describing specific embodiments, and are not intended to limit the present disclosure. The singular forms "a", "said" and "the" used in the embodiments of the present disclosure and the appended claims are also intended to include plural forms, unless the context clearly indicates other meanings.

It should be noted that the directional words such as "upper", "lower", "left", and "right" described in the embodiments of the present disclosure are described at the angles shown in the drawings and should not be understood as limiting the embodiments of the present disclosure. In addition, in the context, it should also be understood that when it is mentioned that an element is formed "on" or "under" another element, it can not only be formed directly "on" or "under" another element, but also be formed "on" or "under" another element indirectly through an intermediate element.

At present, there are two main treatment methods for mitral regurgitation: medication and surgery. The surgical treatment is divided into edge-to-edge repair, valve repair and chord repair. For valve repair, multiple groups of anchors are inserted into the valve ring, and each group of anchors is locked by multiple lockers to achieve the overall repair of the valve. However, the internal situation of the heart valve is not visible during treatment, and the locking force is controlled by the doctor's experience. However, locking each group of anchors one by one cannot ensure that the locking force is consistent each time, resulting in an irregular shape of the repaired valve ring, which leads to uneven valve closure along the valve commissure. Tighter closure will reduce blood flow and cause insufficient blood supply, while looser closure will not achieve the purpose of treating reflux.

Figure 2:
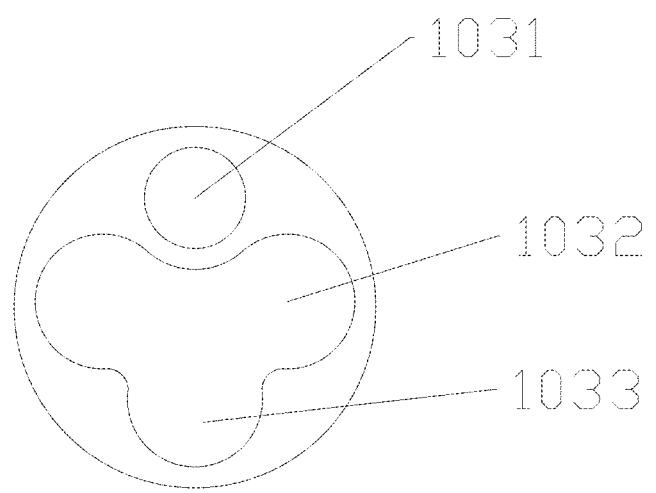
FIG. 2 schematically shows a cross-sectional view of a multi-lumen tube according to an embodiment of the present disclosure.

FIG. 1 schematically shows a schematic diagram of the structure of a delivery system according to an embodiment of the present disclosure, and FIG. 2 schematically shows a cross-sectional view of a multi-lumen tube according to an embodiment of the present disclosure. As shown in FIG. 1 and FIG. 2, a delivery system for valve repair according to the present disclosure includes a first delivery assembly 10 and a second delivery assembly 20.

The first delivery assembly 10 includes a first wire locker control device 101 and a first nailing control device 102. One end of the first wire locker control device 101 is fixedly connected to the multi-lumen tube 103, and the other end is detachably connected to the first nailing control device 102. The first nailing control device 102 is configured to control the first nail driving device to drive nails, and the first wire locker control device 101 is configured to control the first wire locker to lock the first nail driving device.

The second delivery assembly 20 is detachably connected to the first wire locker control device 101. The second delivery assembly 20 includes a second wire locker control device 201 and a second nailing control device 202. The second nailing control device 202 is configured to control the second nail driving device to drive nails. The second wire locker control device 201 is configured to control the second wire locker to lock the second nail driving device.

The multi-lumen tube 103 includes a first lumen 1031, a second lumen 1032 and a third lumen 1033 arranged axially therein. The first lumen 1031 is used for the first wire locker to enter, the second lumen 1032 is used for the first nail driver and the second nail driver to enter respectively, and the third lumen 1033 is used for the second wire locker to enter.

The delivery system is configured to allow the first wire locker and the second wire locker to synchronously lock the first nail driver and the second nail driver through the first lumen 1031 and the third lumen 1033.

Specifically, the first delivery assembly 10 includes a first wire locker control device 101 and a first nailing control device 102. One end of the first wire locker control device 101 is detachably connected to the first nailing control device 102 and the second delivery assembly 20, and the other end is fixedly connected to the multi-lumen tube 103.

When the delivery system is used, the first nailing control device 102 is connected to the first wire locker control device 101, so that the first wire locker penetrates into the first lumen 1031 of the multi-lumen tube 103, and the first nailing device penetrates into the second lumen 1032. When the first nailing device completes the nailing operation, the first nailing control device 102 and the first wire locker control device 101 are disassembled, and the second delivery assembly 20 is installed with the first wire locker control device 101, so that the second wire locker in the second wire locker control device 201 penetrates into the third lumen 1033, and the second nailing device in the second nailing control device 202 penetrates into the second lumen 1032. At this time, the first wire locker penetrates into the first lumen 1031, the second nailing device penetrates into the second lumen 1032, and the second wire locker penetrates into the third lumen 1033.

When the second nailing device completes the nailing operation, the first wire locker control device 101 and the second wire locker control device 201 are synchronously controlled to respectively control the first wire locker to lock the first nailing device and the second wire locker to lock the second nailing device, thereby synchronously completing two sets of locking operations.

With such arrangement, when the doctor synchronously controls the two sets of wire lockers for locking, the locking degrees of the two sets of wire lockers are adjusted in real time by comparing the control degrees of the two sets of wire lockers, so that the locking forces of the two sets of nailing devices are consistent or similar, thereby making the overall shape of the heart valve regular, solving the problem that the doctor cannot refer to each other when locking separately and cannot ensure the consistency of the locking forces twice, resulting in irregular shape of the repaired heart valve and affecting the subsequent recovery degree.

Figure 3:
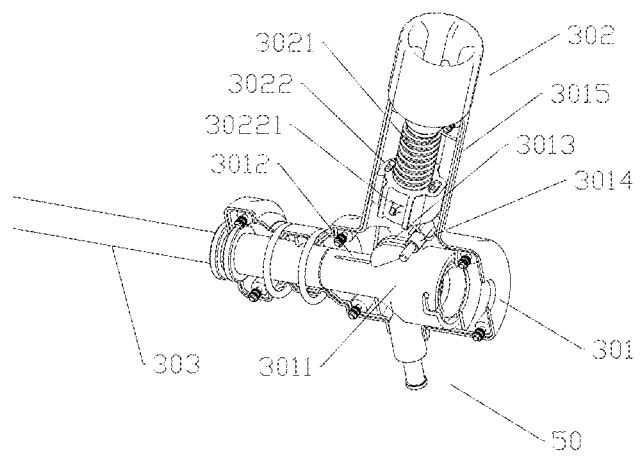
FIG. 3 schematically shows a schematic diagram of a structure of a sheath tube bending-adjustment assembly according to an embodiment of the present disclosure.

Further, FIG. 3 schematically shows a schematic diagram of the structure of a sheath tube bending-adjustment assembly according to an embodiment of the present disclosure. As shown in FIG. 1 and FIG. 3, the delivery system for valve repair according to the present disclosure further includes a sheath tube bending-adjustment assembly 30 and a dilation tube 40.

The sheath tube bending assembly 30 includes a first mounting bracket 301 and a first adjustment structure 302. The first adjustment structure 302 is arranged on the side of the first mounting bracket 301 to be used for bending the sheath tube 303. One end of the first mounting bracket 301 is connected to the sheath tube 303, and the other end is connected to the first wire locker control device 101.

The multi-lumen tube 103 passes through the first mounting bracket 301 and through the sheath tube 303.

Specifically, a first auxiliary connecting piece 3011 is provided in the first mounting bracket 301. The sheath tube 303 is inserted into the first mounting bracket 301 and fixedly connected to one end of the first auxiliary connecting piece 3011, and the other end of the first auxiliary connecting piece 3011 is used for inserting the dilation tube 40 and the first wire locker control device 101, so that the whole is assembled.

A first through hole 3012 and a first groove 3013 are provided on the side wall of the first auxiliary connecting piece 3011. A guide column 3014 is provided on the side wall of the first mounting bracket 301. The first through hole 3012 penetrates the side wall of the first auxiliary connecting piece 3011, and the bending guide wire on the sheath tube 303 can be led out of the first auxiliary connecting piece 3011 through the first through hole 3012.

The first groove 3013 extends in the axial direction. The first groove 3013 and the first through hole 3012 are on the same axis. After the bending guide wire in the sheath tube 303 is led out through the first through hole 3012, it is inserted from one end of the first groove 3013 and passes through the other end of the first groove 3013.

The guide column 3014 is arranged near the other end of the first groove 3013, and the guide column 3014 extends in the radial direction. When the bending adjustment guide wire passes through the other end of the first groove 3013, it is wrapped around the side wall of the guide column 3014. The side wall of the guide column 3014 guides the bending adjustment guide wire of the sheath tube 303 so that the bending adjustment guide wire of the sheath tube 303 changes from extending in the axial direction to extending in the radial direction, and then is fixedly connected to the first adjustment structure 302 located on the side of the first mounting bracket 301. The first adjustment structure 302 can make the bending adjustment guide wire move back and forth in the radial direction, and then the bending of the sheath tube 303 is achieved by pulling the bending adjustment guide wire.

The first mounting bracket 301 further includes a first housing 3015 located at a side of the first mounting bracket 301 and extending outwards. The first adjustment structure 302 is inserted into the first housing 3015 and fixedly connected to the bending adjustment guide wire.

The first adjustment structure 302 includes a first rotating member 3021 and a second rotating member 3022. The second rotating member 3022 is sleeved on the first rotating member 3021, and the two are threadedly connected. A first protrusion 30221 is provided on the circumferential side wall of the second rotating member 3022. A second groove 30151 extending along the axial direction of the first housing 3015 is provided on the first housing 3015. The second groove 30151 penetrates the side wall of the first housing 3015. The first protrusion 30221 is inserted into the second groove 30151 and is slidably connected thereto.

When the first rotating member 3021 is controlled to rotate, the second rotating member 3022 sleeved thereon is limited by the mutual positioning between the first protrusion 30221 and the second groove 30151 to achieve axial movement. The bending adjustment guide wire of the sheath 303 is fixedly connected to the second rotating member 3022. When the second rotating member 3022 moves, the bending adjustment guide wire will be pulled synchronously, thereby realizing the bending operation of the sheath tube 303.

In this way, by setting the first adjustment structure 302 for bending sheath 303 on the side of the first mounting bracket 301, the overall length of the sheath tube bending-adjustment assembly 30 can be shortened, and the length of the wire locker spring tube and the nailing bending-adjustment tube can be reduced to a certain extent. The shorter the length of the wire locker spring tube and the nailing bending-adjustment tube is, the higher the control accuracy of the end control of the wire locker spring tube and the nailing bending-adjustment tube is, which can achieve more precise control during surgery.

Furthermore, an injection channel 50 is also provided on the side of the first auxiliary connecting member 3011, and the injection channel 50 penetrates through the first mounting bracket 301. The injection channel 50 is configured to inject sealing liquid to seal the internal space of the first auxiliary connecting member 3011 to prevent external air from entering the human body through the sheath tube 303, or blood in the human body from flowing out through the sheath tube 303.

Furthermore, the dilation tube 40 is detachably connected to the sheath tube bending-adjustment assembly 30, and the dilation tube 40 can be inserted into the sheath tube 303 and partially extend out of the sheath tube 303.

The insertion end of the dilation tube 40 is set to be conical, which is easier to penetrate the body tissue, guide the insertion of the sheath tube 303, and provide an insertion path for the sheath tube 303. After the dilation tube completes the corresponding operation, it is disassembled from the sheath tube bending-adjustment assembly 30, and the first delivery assembly 10 and the sheath tube bending-adjustment assembly 30 are installed to complete the subsequent valve repair operation.

Figure 4:
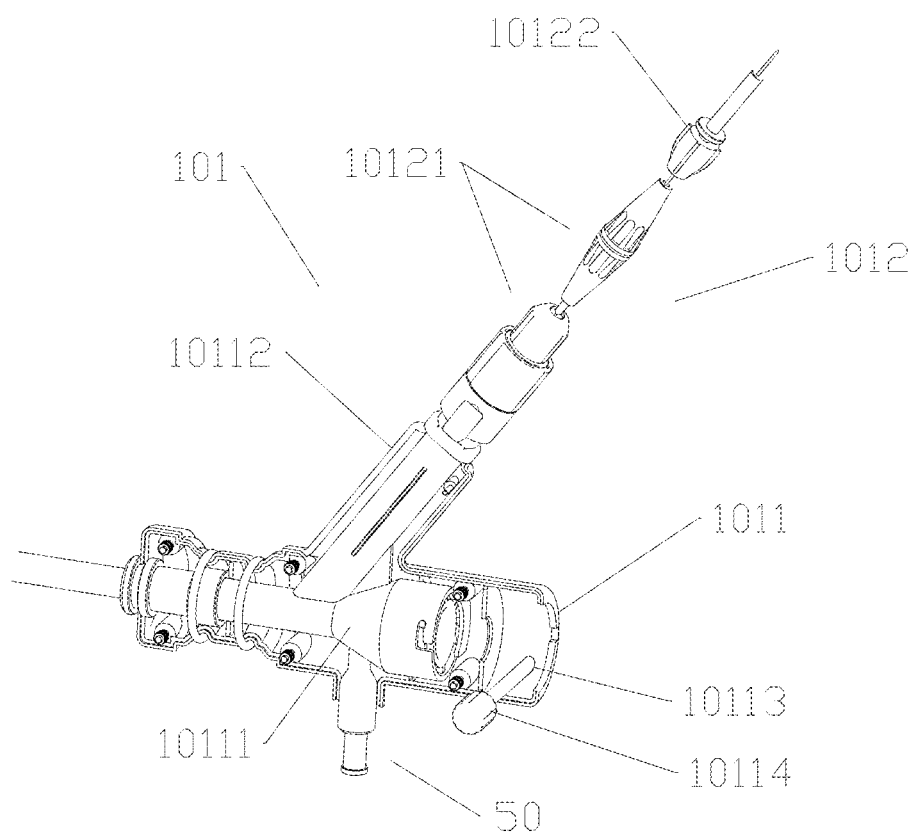
FIG. 4 schematically shows a schematic diagram of a structure of a first wire lock control device according to an embodiment of the present disclosure.

Further, FIG. 4 schematically shows a schematic diagram of a structure of a first wire locker control device according to an embodiment of the present disclosure, as shown in FIG. 4:

the first wire locker control device 101 includes a second mounting bracket 1011 and a second adjustment structure 1012. One end of the second mounting bracket 1011 is connected to the multi-lumen tube 103, and the other end is connected to the first nailing control device 102 or the second delivery assembly 20. The second adjustment structure 1012 is fixedly connected to the side of the second mounting bracket 1011. The second adjustment structure 1012 is configured to control the axial movement and circumferential rotation of the first wire locker.

The first wire locker passes through the second adjustment structure 1012 and the second mounting bracket 1011 in sequence.

Specifically, a second auxiliary connecting piece 10111 is provided in the second mounting bracket 1011. The multi-lumen tube 103 is inserted into the second mounting bracket 1011 and fixedly connected to one end of the second auxiliary connecting piece 10111. The first nailing control device 102 and the second delivery assembly 20 are detachably connected to the other end of the second auxiliary connecting piece 10111.

The second mounting bracket 1011 further includes a second housing 10112 disposed at a side thereof. The second housing 10112 extends in a radial direction. The second adjustment structure 1012 is mounted on the second housing 10112. A first wire locker spring tube is disposed in the second adjustment structure 1012. The first wire locker spring tube penetrates the second adjustment structure 1012, passes through the second housing 10112 and enters into the first lumen 1031 of the multi-lumen tube 103.

A first wire locker is arranged in the first wire locker spring tube, and the axial movement and circumferential rotation of the first wire locker spring tube can be achieved through the control of the second adjustment structure 1012, thereby achieving the locking operation of the first wire locker.

A first steel cable is arranged in the first wire locker spring tube, and an end portion of the first steel cable is detachably connected to the first wire locker. The second adjustment structure 1012 includes a first control member 10121 and a second control member 10122. The first control member 10121 is sleeved on the first wire locker spring tube, and the second control member 10122 is sleeved on the first steel cable. The first control member 10121 can control the axial movement and circumferential rotation of the first wire locker spring tube. The second control member 10122 can control the axial movement and circumferential rotation of the first steel cable, and can control the disassembly of the first steel cable and the first wire locker. When the first wire locker completes the locking operation, the first steel cable and the first wire locker are controlled to be disassembled, and then the first wire locker spring tube and the first steel cable are controlled to be synchronously withdrawn from the body to complete the surgical operation.

An injection channel 50 is also provided on the side of the second auxiliary connecting piece 10111. The injection channel 50 penetrates through the second mounting bracket 1011. The injection channel 50 is configured to inject sealing liquid to seal the internal space of the second auxiliary connecting piece 10111 to prevent external air from entering the human body through the multi-lumen tube 103, or blood from flowing out of the human body.

In this way, by arranging the second adjustment structure 1012 on the side of the first mounting bracket 301, the length of the entire device can also be shortened, thereby reducing the overall length of the wire locker spring tube and the overall length of the nailing bending-adjustment tube to achieve more precise control.

Figure 5:
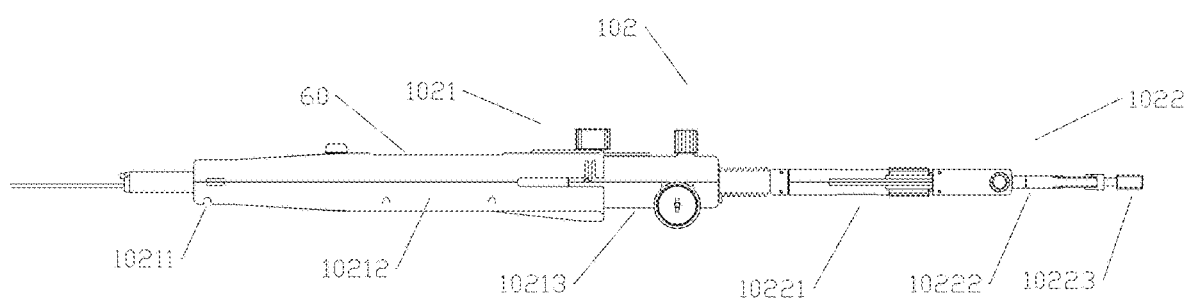
FIG. 5 schematically shows a schematic diagram of a structure of a first nailing control device according to an embodiment of the present disclosure.

Further, FIG. 5 schematically shows a schematic diagram of a structure of a first nailing control device according to an embodiment of the present disclosure, as shown in FIG. 5:

the first nailing control device 102 includes a third mounting bracket 1021 and a third adjustment structure 1022. One end of the third mounting bracket 1021 is connected to the second mounting bracket 1011, and the other end is connected to the third adjustment structure 1022.

The first nailing device passes through the third adjustment structure 1022, the third mounting bracket 1021 and the second mounting bracket 1011 in sequence. The third adjustment structure 1022 is configured to control the axial movement and circumferential rotation of the first nailing device.

Specifically, a first limiting hole 10113 is provided on the side wall of the second mounting bracket 1011, and a first limiting groove 10211 is provided on the side wall of the third mounting bracket 1021. When the first nailing control device 102 and the first wire locker control device 101 are installed, the first limiting groove 10211 and the first limiting hole 10113 are provided correspondingly. The first limiting member 10114 is inserted into the first limiting groove 10211 through the first limiting hole 10113, so as to limit the movement of the third mounting bracket 1021 relative to the second mounting bracket 1011, thereby realizing the fixed connection between the first wire locker control device 101 and the first nailing control device 102.

Furthermore, a first nailing bending-adjustment tube is provided in the first nailing control device 102, and a first nailing device is provided in the first nailing bending-adjustment tube. When the first nailing control device 102 and the first wire locker control device are installed, the first nailing bending-adjustment tube extends into the second lumen 1032 of the multi-lumen tube 103, and the first nailing control device 102 controls the axial movement, circumferential rotation and end bending of the first nailing bending-adjustment tube, so that the internal first nailing device is nailed into the valve tissue to realize the nailing operation.

The third mounting bracket 1021 includes a third housing 10212 and a fourth housing 10213. The third housing 10212 is slidably connected to the fourth housing 10213, the third housing 10212 is connected to the second mounting bracket 1011. The first limiting groove 10211 is arranged on the side wall of the third shell 10212.

The third adjustment structure 1022 is connected to the fourth housing 10213. When the fourth housing 10213 slides relative to the third housing 10212, the third adjustment structure 1022 installed on the fourth housing 10213 can move synchronously as a whole.

A first nailing spring-tube is arranged in the first nailing bending-adjustment tube. A second steel cable is arranged in the first nailing spring-tube. The end of the second steel cable is detachably connected to the first nailing device. The third adjustment structure 1022 includes a third control member 10221, a fourth control member 10222 and a fifth control member 10223. The third control member 10221 is sleeved with the first nailing bending-adjustment tube, and can control the axial movement, circumferential rotation and bending of the end of the first nailing bending-adjustment tube. The fourth control member 10222 is sleeved with the first nailing spring-tube, and can control the axial movement and circumferential rotation of the first nailing spring-tube. The fifth control member 10223 is sleeved with the second steel cable, and can control the axial movement and circumferential rotation of the second steel cable.

When performing the nailing operation, the third control member 10221 and the fourth control member 10222 are used to control the first nailing bending-adjustment tube and the first nailing spring-tube to move to the nailing position, and the fifth control member 10223 is used to control the second steel cable to rotate circumferentially, so that the first nailing device at the end is nailed into the valve tissue. After completion, the second steel cable is controlled to be disassembled from the first nailing device, and the first nailing bending-adjustment tube and the first nailing spring-tube are controlled to be withdrawn from the body for subsequent operations.

Figure 6:
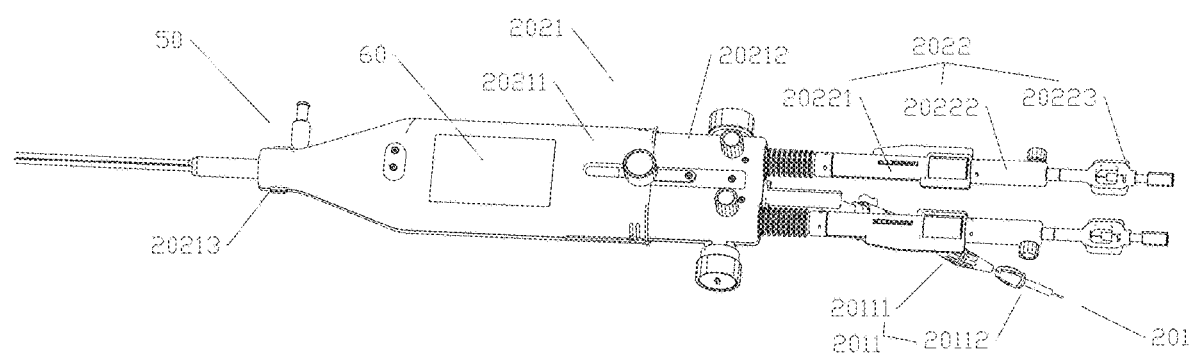
FIG. 6 schematically shows a schematic diagram of a structure of a second delivery assembly according to an embodiment of the present disclosure.

Further, FIG. 6 schematically shows a schematic diagram of a structure of a second delivery assembly according to an embodiment of the present disclosure, as shown in FIG. 6: the second delivery assembly 20 includes a second wire locker control device 201 and a second nailing control device 202. The second wire locker control device 201 is arranged on the housing of the second nailing control device 202.

When the second delivery assembly 20 is installed with the first wire locker device 101, the second nailing control device 202 is connected with the first wire locker device 101.

After the first nailing operation of the first nailing device is completed, the first nailing control device 102 and the first wire locker control device 101 are disassembled, and the first nailing bending-adjustment tube is removed from the second lumen 1032 of the multi-lumen tube 103. At this time, the first nailing device is in the human body, and the first wire locker spring-tube is still in the first lumen 1031 of the multi-lumen tube 103, and the first nailing device is not locked.

At this time, the second nailing control device 202 is installed with the first wire locker control device 101, the second nailing bending-adjustment tube in the second nailing control device 202 is extended into the second lumen 1032, and the second wire locker spring-tube in the second wire locker control device 201 is extended into the third lumen 1033 of the multi-lumen tube 103. When the second nailing control device 202 controls the second nailing device to complete the nailing operation, the first wire locker control device 101 and the second wire locker control device 201 are synchronously controlled to respectively make the first wire locker lock the first nailing device and the second wire locker lock the second nailing device.

In this way, by arranging the first lumen 1031, the second lumen 1032, and the third lumen 1033 in the multi-lumen tube 103, when the first wire locker control device 101 and the second wire locker control device 201 are synchronously operated, the specific locking force of each wire locker can be clearly perceived by comparing the two controls, and whether the locking force of a certain wire locker is larger or smaller can be perceived, and real-time adjustments can be achieved, thereby making the final shape of the valve regular after repair.

Furthermore, the second nailing control device 202 includes a fourth mounting bracket 2021 and a fourth adjustment structure 2022. One end of the fourth mounting bracket 2021 is connected to the second mounting bracket 1011, and the other end is connected to the fourth adjustment structure 2022 and the second wire locker control device 201.

The second nailing device passes through the fourth adjustment structure 2022, the fourth mounting bracket 2021 and the second mounting bracket 1011 in sequence. The fourth adjustment structure 2022 is configured to control the axial movement and circumferential rotation of the second nailing device.

Specifically, the fourth mounting bracket 2021 has the same structure as the third mounting bracket 1021, and is also provided with a fifth housing 20211 and a sixth housing 20212. The sixth housing 20212 is slidably connected to the fifth housing 20211. The fourth adjustment structure 2022 and the second wire locker control device 201 are installed on the sixth housing 20212. When the sixth housing 20212 moves relative to the fifth housing 20211, the fourth adjustment structure 2022 and the second wire locker control device 201 can be controlled to move synchronously.

A second limiting groove 20213 is provided on the side wall of the fifth housing 20211. When the fifth housing 20211 and the second mounting bracket 1011 are installed, the first limiting member 10114 is inserted into the first limiting hole 10113 and the second limiting groove 20213 to achieve fixed connection between the fourth mounting bracket 2021 and the second mounting bracket 1011.

The fourth adjustment structure 2022 has the same structure as the third adjustment structure 1022. The second nailing bending-adjustment tube passes through the fourth adjustment structure 2022 and the fourth mounting bracket 2021 and enters the second lumen tube 1032 of the multi-lumen tube 103. A second nailing spring-tube is arranged in the second nailing bending-adjustment tube. A third steel cable is arranged in the second nailing spring-tube. The end of the third steel cable is detachably connected to a second nailing device.

The fourth adjustment structure 2022 includes a sixth control member 20221, a seventh control member 20222 and an eighth control member 20223. The sixth control member 20221 is sleeved on the second nailing bending-adjustment tube, which can control the axial movement, circumferential rotation and end bending of the second nailing bending-adjustment tube. The seventh control member 20222 is sleeved on the second nailing spring-tube, which can control the axial movement and circumferential rotation of the second nailing spring-tube. The eighth control member 20223 is sleeved on the third steel cable, which can control the axial movement and circumferential rotation of the third steel cable to realize the nailing operation of the second nailing device.

Furthermore, the second wire lock control device 201 includes a fifth adjustment structure 2011, and the fifth adjustment structure 2011 has the same structure as the second adjustment structure 1012.

A second wire locker spring-tube is arranged in the second wire locker control device 201. The second wire locker spring-tube passes through the fifth adjustment structure 2011, and passes through the fourth mounting bracket 2021 and the second mounting bracket 1011 and extends into the third lumen 1033 of the multi-lumen tube 103.

A fourth steel cable is arranged in the second wire locker spring-tube. A second wire locker is arranged at the end of the fourth steel cable. The fifth adjustment structure 2011 includes a ninth control member 20111 and a tenth control member 20112. The ninth control member 20111 is sleeved on the second wire locker spring-tube, and can control the axial movement and circumferential rotation of the second wire locker spring-tube. The tenth control member 20112 is sleeved on the fourth steel cable, and can control the axial movement and circumferential rotation of the fourth steel cable, so as to realize the operation of the second wire locker locking the second nailing device.

Furthermore, an observation window 60 is provided on the third mounting bracket 1021 and the fourth mounting bracket 2021. The observation window 60 is made of a transparent material. The first nailing bending-adjustment tube in the first nailing control device 102 can pass through the observation window 60, and the second nailing bending-adjustment tube and the second wire locker spring-tube in the second nailing control device 202 can pass through the observation window 60, so that the doctor can check the axial movement distance of the tube.

Furthermore, the present disclosure also provides a control method of a delivery system, which is applied to the above-mentioned delivery system for valve repair, and the method includes:
- S01: inserting the dilation tube 40 into the sheath tube bending-adjustment assembly 30, and guiding the sheath tube 303 into the body;
- S02: disassembling the dilation tube 40, installing the first wire locker control device 101 and the sheath tube bending-adjustment assembly 30 to insert the multi-lumen tube 103 into the sheath tube 303, and insert the first wire locker spring-tube into the first lumen 1031 of the multi-lumen tube 103;
- S03: installing the first nailing control device 102 and the first wire locker control device 101, so that the first nailing bending-adjustment tube is inserted into the second lumen tube 1032 of the multi-lumen tube 103;
- S04: controlling the first nailing control device 102 to nail the first nailing device in the first nailing bending-adjustment tube into the valve tissue, disassembling the first nailing control device 102 and the first wire locker control device 101, and withdrawing the first nailing bending-adjustment tube from the second lumen 1032;
- S05: installing the second nailing control device 202 and the first wire locker control device 101, insert the second nail driving bending adjustment tube into the second lumen 1032, and insert the second wire locker spring tube into the third lumen 1033;
- S06: controlling the second nailing control device 202 to drive the second nailing device in the second nailing bending-adjustment tube into the valve tissue;
- S07: synchronously controlling the first wire locker control device 101 and the second wire locker control device 201 to respectively make the first wire locker in the first wire locker spring-tube lock the first nailing device and the second wire locker in the second wire locker spring-tube lock the second nailing device with the same or similar locking force;
- S08: withdrawing the sheath tube bending-adjustment assembly 30 from the body, and disassembling the connections among the sheath tube bending-adjustment assembly 30, the first wire locker 101, and the second nailing control device 202 to complete the surgical operation.

With such arrangement, through the above control method, the synchronous locking of the two sets of nailing devices can be achieved, which solves the problem that when the locking of the nailing devices is controlled individually, there is no comparison between the two sets of nailing devices, and the locking force of each set cannot be referenced to each other for real-time adjustment, resulting in irregular shape of the repaired valve. Through the scheme of the present disclosure, the sheath adjustment assembly includes a first mounting bracket and a first adjustment structure, and the first adjustment structure is arranged on the side of the first mounting bracket. In this way, the overall length of the sheath adjustment device can be reduced, thereby shortening the length of the nailing and bending adjustment tube and the wire locking spring tube. The shorter the length of the nailing and bending adjustment tube and the wire locking spring tube, the higher the accuracy of the first delivery assembly and the second delivery assembly in controlling their movement and bending.

Moreover, after step S07, if a third set of nailing is required on the valve, the first wire locking control device 101 and the sheath tube bending-adjustment assembly 30 can be disassembled, and the third delivery assembly having a third wire locker control device and a third nailing control device and the sheath tube bending-adjustment assembly 30 can be installed to complete the third set of nailing operation.

To sum up, through the scheme of the present disclosure, when the first nailing device completes nailing, the first wire locker can remain in the first lumen 1031 of the multi-lumen tube 103. When the second nailing device nails, the second wire locker is located in the third lumen 1033. When the second nailing device completes nailing, the doctor can synchronously control the first wire locker control device 101 and the second wire locker control device 201 to control the first wire locker and the second wire locker to respectively lock the first nailing device and the second nailing device with the same or similar locking force, so that the shape of the repaired valve is regular.

The above description is only a preferred embodiment of the present disclosure and an explanation of the technical principles used. Those skilled in the art should understand that the scope of the disclosure involved in the present disclosure is not limited to the technical solution formed by a specific combination of the above technical features, but should also cover other technical solutions formed by any combination of the above technical features or their equivalent features without departing from the inventive concept. For example, the above features are replaced with (but not limited to) technical features with similar functions disclosed in the present disclosure.

What is claimed is:

1. A delivery system for valve repair, comprising:
   a first delivery assembly and a second delivery assembly;
   wherein the first delivery assembly comprises a first wire locker control device and a first nailing control device, one end of the first wire locker control device is fixedly connected to a multi-lumen tube, and the other end of the first wire locker control device is detachably connected to the first nailing control device, the first nailing control device is configured to control a first nailing device to nail, and the first wire locker control device is configured to control a first wire locker to lock the first nailing device;
   the second delivery assembly is detachably connected to the first wire locker control device, the second delivery assembly comprises a second wire locker control device and a second nailing control device, the second nailing control device is configured to control a second nailing device to nail, and the second wire locker control device is configured to control a second wire locker to lock the second nailing device;
   the second wire locker control device is arranged on a housing of the second nailing control device, and the second nailing control device is detachably connected to the first wire locker control device; based on that the second nailing control device is connected to the first wire locker control device, the first nailing control device is detached from the first wire locker control device;
   the multi-lumen tube comprises a first lumen, a second lumen and a third lumen which are arranged axially, the first lumen is used for the first wire locker to enter, the second lumen is used for the first nailing device and the second nailing device to enter respectively, and the third lumen is used for the second wire locker to enter;
   wherein the delivery system for valve repair is configured to enable the first wire locker and the second wire locker to synchronously lock the first nailing device and the second nailing device through the first lumen and the third lumen.

2. The delivery system for valve repair according to claim 1, further comprising a sheath tube bending-adjustment assembly;
   wherein the sheath tube bending-adjustment assembly comprises a first mounting bracket and a first adjustment structure, wherein the first adjustment structure is arranged on a side of the first mounting bracket for adjusting a bending of a sheath tube, one end of the first mounting bracket is connected to the sheath tube, and the other end of the first mounting bracket is connected to the first wire locker control device;
   the multi-lumen tube passes through the first mounting bracket and passes through the sheath tube.

3. The delivery system for valve repair according to claim 1, wherein the first wire locker control device comprises a second mounting bracket and a second adjustment structure, one end of the second mounting bracket is connected to the multi-lumen tube, and the other end of the second mounting bracket is connected to the first nailing control device or the second delivery assembly, the second adjustment structure is fixedly connected to a side of the second mounting bracket, and the second adjustment structure is configured to control an axial movement and a circumferential rotation of the first wire locker;
   wherein the first wire lock passes through the second adjustment structure and the second mounting bracket in sequence.

4. The delivery system for valve repair according to claim 3, wherein the first nailing control device comprises a third mounting bracket and a third adjustment structure, one end of the third mounting bracket is connected to the second mounting bracket, and the other end of the third mounting bracket is connected to the third adjustment structure;
   wherein the first nailing device passes through the third adjustment structure, the third mounting bracket and the second mounting bracket in sequence, and the third adjustment structure is configured to control an axial movement and a circumferential rotation of the first nailing device.

5. The delivery system for valve repair according to claim 4, wherein the second nailing control device comprises a fourth mounting bracket and a fourth adjustment structure, one end of the fourth mounting bracket is connected to the second mounting bracket, and the other end of the fourth mounting bracket is connected to the fourth adjustment structure and the second wire locker control device;
   wherein the second nailing device passes through the fourth adjustment structure, the fourth mounting bracket and the second mounting bracket in sequence, and the fourth adjustment structure is configured to control an axial movement and a circumferential rotation of the second nailing device.

6. The delivery system for valve repair according to claim 5, wherein the second wire locker control device comprises a fifth adjustment structure, and the fifth adjustment structure is connected to the fourth mounting bracket;
   wherein the second wire locker passes through the fifth adjustment structure, the fourth mounting bracket and the second mounting bracket in sequence, and the fifth adjustment structure is configured to control an axial movement and a circumferential rotation of the second wire locker.

7. The delivery system for valve repair according to claim 5, wherein a first limiting hole is arranged on a side wall of the second mounting bracket, the first limiting hole penetrates the side wall of the second mounting bracket, a first limiting groove is arranged on a side wall of the third mounting bracket, and a second limiting groove is arranged on a side wall of the fourth mounting bracket;
   based on that the third mounting bracket or the fourth mounting bracket is connected to the second mounting bracket, a first limiting member is inserted into the first limiting groove or the second limiting groove through the first limiting hole, and the first limiting member is configured to limit a movement of the third mounting bracket or a movement of the fourth mounting bracket.

8. The delivery system for valve repair according to claim 2, further comprising a dilation tube, wherein the dilation tube is detachably connected to the sheath tube bending-adjustment assembly.

9. The delivery system for valve repair according to claim 5, wherein injection channels are respectively arranged on the second mounting bracket, the third mounting bracket and the fourth mounting bracket, and the injection channels are configured to inject sealing liquid to seal an internal space of the multi-lumen tube.

10. The delivery system for valve repair according to claim 5, wherein observation windows are respectively arranged on the third mounting bracket and the fourth mounting bracket, and the observation windows are made of transparent material.

* * * * *